United States Patent (10) Patent No.: US 9,228,992 B2
Kato et al. (45) Date of Patent: Jan. 5, 2016

(54) ELECTRIC INSULATING OIL INSPECTION METHOD, ELECTRIC INSULATING OIL TREATMENT METHOD, AND OIL-FILLED ELECTRIC DEVICE MAINTENANCE METHOD

(75) Inventors: Fukutaro Kato, Chiyoda-ku (JP); Eiichi Nagao, Chiyoda-ku (JP); Tsuyoshi Amimoto, Chiyoda-ku (JP); Satoru Toyama, Chiyoda-ku (JP); Kota Mizuno, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 237 days.

(21) Appl. No.: 13/816,261

(22) PCT Filed: Dec. 13, 2010

(86) PCT No.: PCT/JP2010/072376
§ 371 (c)(1),
(2), (4) Date: Feb. 11, 2013

(87) PCT Pub. No.: WO2012/081073
PCT Pub. Date: Jun. 21, 2012

(65) Prior Publication Data
US 2013/0134367 A1 May 30, 2013

(51) Int. Cl.
*G01N 33/28* (2006.01)
(52) U.S. Cl.
CPC .......... *G01N 33/2835* (2013.01); *G01N 33/287* (2013.01)
(58) Field of Classification Search
CPC .................................................. G01N 33/2835
USPC ....................................................... 252/570
See application file for complete search history.

(56) References Cited

U.S. PATENT DOCUMENTS

| 3,419,497 | A | * | 12/1968 | Rocchini et al. | 252/578 |
| 3,904,512 | A | * | 9/1975 | Clark | 208/182 |
| 3,957,628 | A | * | 5/1976 | Siskin et al. | 208/223 |
| 2008/0135277 | A1 | * | 6/2008 | Gafvert | 174/25 C |
| 2008/0251424 | A1 | * | 10/2008 | Dahlund | 208/246 |
| 2010/0192673 | A1 | * | 8/2010 | Toyama et al. | 73/23.37 |
| 2011/0246149 | A1 | * | 10/2011 | Toyama et al. | 703/2 |

FOREIGN PATENT DOCUMENTS

| CN | 1460860 A | 12/2003 |
| CN | 2589048 Y | 12/2003 |
| CN | 101142305 A | 3/2008 |
| JP | 59-23404 A | 2/1984 |
| JP | 59-217901 A | 12/1984 |
| JP | 63-257112 A | 10/1988 |
| JP | 2-151764 A | 6/1990 |
| JP | 2001-311083 A | 11/2001 |
| JP | 2010-27634 A | 2/2010 |
| WO | 2007/096709 A2 | 8/2007 |
| WO | 2008/003790 A1 | 1/2008 |
| WO | WO 2010/073748 A1 | 7/2010 |

OTHER PUBLICATIONS

Amimoto et al. IEEE Transactions on Dielectrics and Electrical Insulation. vol. 16, No. I; Feb. 2000.*
Electrical Facilities Instructions, Standards and Technics. 2000.*
Office Action issued on Jun. 27, 2014, by the Chinese Patent Office in corresponding Chinese Patent Application No. 201080069365.X and an English translation of the Office Action. (17 pages).
Lian et al., "Causes and Countermeasures for Sulfur Corrosion of Insulation Oil in Transformers", Fujian Dianli Yu Diangong, Dec. 31, 2008, vol. 28, No. 4, pp. 17-20.
Lu et al., "Sulfur Corrosion in Transfomer Oil and Countermeasures", East China Electric Power, Nov. 2008, vol. 36, No. 11, pp. 39-42.
International Search Report (PCT/ISA/210) issued on Feb. 8, 2011, by the Japanese Patent Office as the International Searching Authority for International Application No. PCT/JP2010/072376.

(Continued)

*Primary Examiner* — Nicole M Buie-Hatcher
*Assistant Examiner* — M. Reza Asdjodi
(74) *Attorney, Agent, or Firm* — Buchanan Ingersoll & Rooney PC

(57) ABSTRACT

The present invention relates to an electric insulating oil inspection method for determining whether or not an inhibitor-consuming substance is present in an electric insulating oil. The inhibitor-consuming substance is such a substance that causes to decrease over time a concentration of an inhibitor which is added to the electric insulating oil to inhibit copper sulfide from being generated on an insulating paper immersed in the electric insulating oil. The electric insulting oil inspection method includes steps of: preserving the electric insulating oil at a predetermined condition, measuring a concentration of the inhibitor, and determining that the inhibitor-consuming substance is present upon condition that a decrement of the concentration of the inhibitor relative to an initial concentration of the inhibitor becomes not less than a specified amount within a predetermined period.

7 Claims, 2 Drawing Sheets

(56) References Cited

OTHER PUBLICATIONS

K. Mizuno et al., Identification of compounds leading to copper sulfide formation on insulating paper in transformers and the degradation of suppressing effect of passivator in insulating oil, The Japan Petroleum Institute Zetsuen'yu Bunkakai Kenkyu Happyokai Yoshishu, Jun. 12, 2009, vol. $29^{th}$, pp. 1-6.

T. Amimoto et al., Duration and Mechanism for Suppressive Effect of Triazole-based Passivators on Copper-sulfide Deposition on Insulating Paper, IEEE Transactions on Dielectrics and Electrical Insulation, vol. 16, No. 1, Feb. 2009, pp. 257-264.

F. Scatiggio et al., Corrosive Sulfur Induced Failures in Oil-Filled Electrical Power Transformers and Shunt Reactors, IEEE Transactions on Power Delivery, vol. 24, No. 3, Jul. 2009, pp. 1240-1248.

Fumihito Saito et al., Investigating Test Method for Copper Sulphide in Transformer Insulation, The Japan Petroleum Institute Zetsuen'yu Bunkakai Kenkyu Happyokai Yoshishu, vol. $28^{th}$, Jun. 2008, pp. 9-13.

Masaki Kataoka, Non-Tribo Oils (3) Electrical Insulating Oils, Journal of Japanese Society of Tribologists, Jul. 15, 1999, vol. 44, No. 7, pp. 512-517.

Motoo Tsuchie et al., Degradation and Cupric Corrosion caused by Corrosive Sulfur in Insulating Oil, The Transactions of the Institute of Electrical Engineers of Japan B, Apr. 1995, vol. 115, No. 4, pp. 388-393.

Cigre WG A2-32, Copper sulphide in transformer insulation, Final Report Brochure 378, 2009 pp. 1-35.

F. Scatiggio et al., Corrosive Sulfur in Insulating Oils: Its Detection and Correlated Power Apparatus Failures, IEEE Transactions on Power Delivery, vol. 23, No. 1, Jan. 2008, pp. 508-509.

S. Toyama et al., Highly Sensitive Detection Method of Dibenzyl Disulfide and the Elucidation of the Mechanism of Copper Sulfide Generation in Insulating Oil, IEEE Transactions on Dielectrics and Electrical Insulation, vol. 16, No. 2, Apr. 2009, pp. 509-515.

* cited by examiner

ELECTRIC INSULATING OIL INSPECTION METHOD, ELECTRIC INSULATING OIL TREATMENT METHOD, AND OIL-FILLED ELECTRIC DEVICE MAINTENANCE METHOD

TECHNICAL FIELD

The present invention relates to an inspection method of an electric insulating oil used in an oil-filled electric device such as an oil-filled transformer or the like, an electric insulating oil treatment method, and an oil-filled electric device maintenance method.

More specifically, the present invention relates to an inspection method for determining whether or not there is present a substance (hereinafter, abbreviated as an inhibitor-consuming substance) which causes a concentration of an inhibitor in the electric insulating oil to decrease over time when the inhibitor is added to the electric insulating oil to inhibit generation of copper sulfide on an insulating paper immersed in the electric insulating oil. Further, the present invention relates to an electric insulating oil treatment method wherein if the inhibitor-consuming substance is determined to be present in the electric insulating oil according to the electric insulating oil inspection method, a filtering treatment such as a clay treatment or the like is conducted on the electric insulating oil to remove the inhibitor-consuming substance from the electric insulating oil so as to revive the inhibitor efficiently. Furthermore, the present invention relates to an oil-filled electric device maintenance method employing such electric insulating oil treatment method.

BACKGROUND ART

In an oil-filled electric device such as an oil-filled transformer or the like, copper coil serves as a conducting medium. The coil is wrapped by an insulating paper to ensure electric insulation, preventing the coil from short-circuiting electrically between adjacent turns.

Meanwhile, the oil-filled transformer is filled with an electric insulating oil generally containing mineral oil or the like. It has been known that the mineral oil or the like contains a very small amount of sulfur ingredient, and the sulfur ingredient reacts with copper coil disposed in the electric insulating oil to generate conductive copper sulfide on a surface of the insulating paper wrapped on the coil. It has been known that the generation of copper sulfide will reduce insulating performance of the insulating paper wrapped on the coil, and even cause the coil to short-circuit between turns, leading to dielectric breakdown (for example, NPL 1).

It has been known that a major causative substance for the generation of copper sulfide is dibenzyl disulfide serving as the sulfur ingredient in the mineral oil (for example, NPL 2). As a generation mechanism of copper sulfide, it has been known that after a complex generated from the reaction of dibenzyl disulfide with copper coil diffuses in the oil and adheres to the insulating paper, it decomposes to generate copper sulfide (for example, NPL 3).

It has been known that inhibiting, on the basis of the generation mechanism mentioned above, the reaction between dibenzyl disulfide and copper coil leads to preventing the generation of copper sulfide; therefore, methods of adding an inhibitor to the electric insulating oil have been widely employed. As the inhibitor, there has been known benzotriazole compound such as 1, 2, 3-benzotriazole (BTA), Irgamet 39 or the like (for example, NPL 4).

After the inhibitor against the generation of copper sulfide is added to the electric insulating oil, the inhibitor reacts with copper coil to form a film on the surface of copper coil. Owing to the formed film, the reaction between dibenzyl disulfide and copper coil is blocked or inhibited; thereby, the generation of copper sulfide can be prevented (for example, NPL 4).

CITATION LIST

Non Patent Literature

NPL 1: CIGRE WG A2-32, "Copper sulphide in transformer insulation," Final Report Brochure 378, 2009

NPL 2: F. Scatiggio, V. Tumiatti, R. Maina, M. Tumiatti, M. Pompilli and R. Bartnikas, "Corrosive Sulfur in Insulating Oils: Its Detection and Correlated Power Apparatus Failures", IEEE Trans. Power Del., Vol. 23, pp. 508-509, 2008

NPL 3: S. Toyama, J. Tanimura, N. Yamada, E. Nagao and T. Amimoto, "Highly Sensitive Detection Method of Dibenzyl Disulfide and the Elucidation of the Mechanism of Copper Sulfide Generation in Insulating Oil", IEEE Transactions on Dielectrics and Electrical Insulation, Vol. 16, No. 2, pp. 509-515, 2009

NPL 4: T. Amimoto, E. Nagao, J. Tanimura, S. Toyama and N. Yamada, "Duration and Mechanism for Suppressive Effect of Triazole-based Passivators on Copper-sulfide Deposition on Insulating Paper", IEEE Transactions on Dielectrics and Electrical Insulation, Vol. 16, No. 1, pp. 257-264, 2009

SUMMARY OF INVENTION

Technical Problem

The inventors of the present invention found out that a concentration of an inhibitor in an electric insulating oil may decrease over time after having conducted periodical analyses for at least 20 years on the concentration of the inhibitor in the electric insulating oil by keeping the electric insulating oil (mineral oil), which is sampled from an actually operating oil-filled transformer and is added with only the inhibitor without any other coexisting material, at a temperature (40° C. to 60° C.) close to an operation temperature of the transformer. On the other hand, in the case where the inhibitor is added to fresh oil, the concentration of the inhibitor is substantially constant without varying over time.

Therefore, it has been discovered that in the case where the electric insulating oil is fresh oil, the concentration of the inhibitor added to the electric insulating oil against the generation of copper sulfide almost does not decrease over time; however, in the case where the electric insulating oil is aged oil, the concentration of the inhibitor may decrease abruptly. The reason therefor has been considered that when the oil-filled electric device undergoes long-term deterioration, a substance (inhibitor-consuming substance) which causes the concentration of the inhibitor in the electric insulating oil to decrease over time is generated in the electric insulating oil, which causes the concentration of the inhibitor in the electric insulating oil to decrease over time.

When the concentration of the inhibitor in the electric insulating oil decreases, the inhibiting effect of the inhibitor for inhibiting the generation of copper sulfide becomes weak; thereby, it is necessary to add an additional inhibitor. However, the addition of a large amount of inhibitor will affect charging characteristics of the oil; thereby, it is not desired to add the inhibitor equal to or more than a predetermined amount. On the other hand, if the inhibitor is added frequently, the power needs to be shut down so as to conduct the adding operation each time; thereby, it is troublesome and may lead to an adverse effect on electric supply. Therefore, in the case where the inhibitor against the generation of copper sulfide is added to aged oil being used in an oil-filled electric device so as to use it continuously, it is desired to add the inhibitor at necessary timings by a minimum requirement.

The present invention has been accomplished in view of the aforementioned problems and it is, therefore, an object of the present invention to provide an inspection method for determining whether an inhibitor-consuming substance is present in an electric insulating oil in order to determine whether it is necessary to add an inhibitor against the generation of copper sulfide into the electric insulating oil so as to use the electric insulating oil in an oil-filled electric device continuously.

Solution to Problem

The prevent invention provides an electric insulating oil inspection method for determining whether or not an inhibitor-consuming substance is present in an electric insulating oil. The inhibitor-consuming substance is such a substance that causes to decrease over time a concentration of an inhibitor which is added to the electric insulating oil to inhibit the generation of copper sulfide on an insulating paper immersed in the electric insulating oil. The electric insulting oil inspection method includes: a first step of preserving the electric insulating oil at a predetermined condition and measuring a concentration of the inhibitor; and a second step of determining that the inhibitor-consuming substance is present upon condition that a decrement of the concentration of the inhibitor relative to an initial concentration thereof becomes not less than a specified amount within a predetermined period.

Advantageous Effects of Invention

According to the present invention, the electric insulating oil is preserved at a predetermined condition and the concentration of the inhibitor is measured, and upon condition that a decrement of the concentration of the inhibitor relative to the initial concentration thereof becomes not less than a specified amount within a predetermined period, it is determined that the inhibitor-consuming substance is present; accordingly, it is possible to predict the temporal variation of the electric insulating oil.

DESCRIPTION OF EMBODIMENTS

[Electric Insulating Oil Inspection Method]

Figure 1:
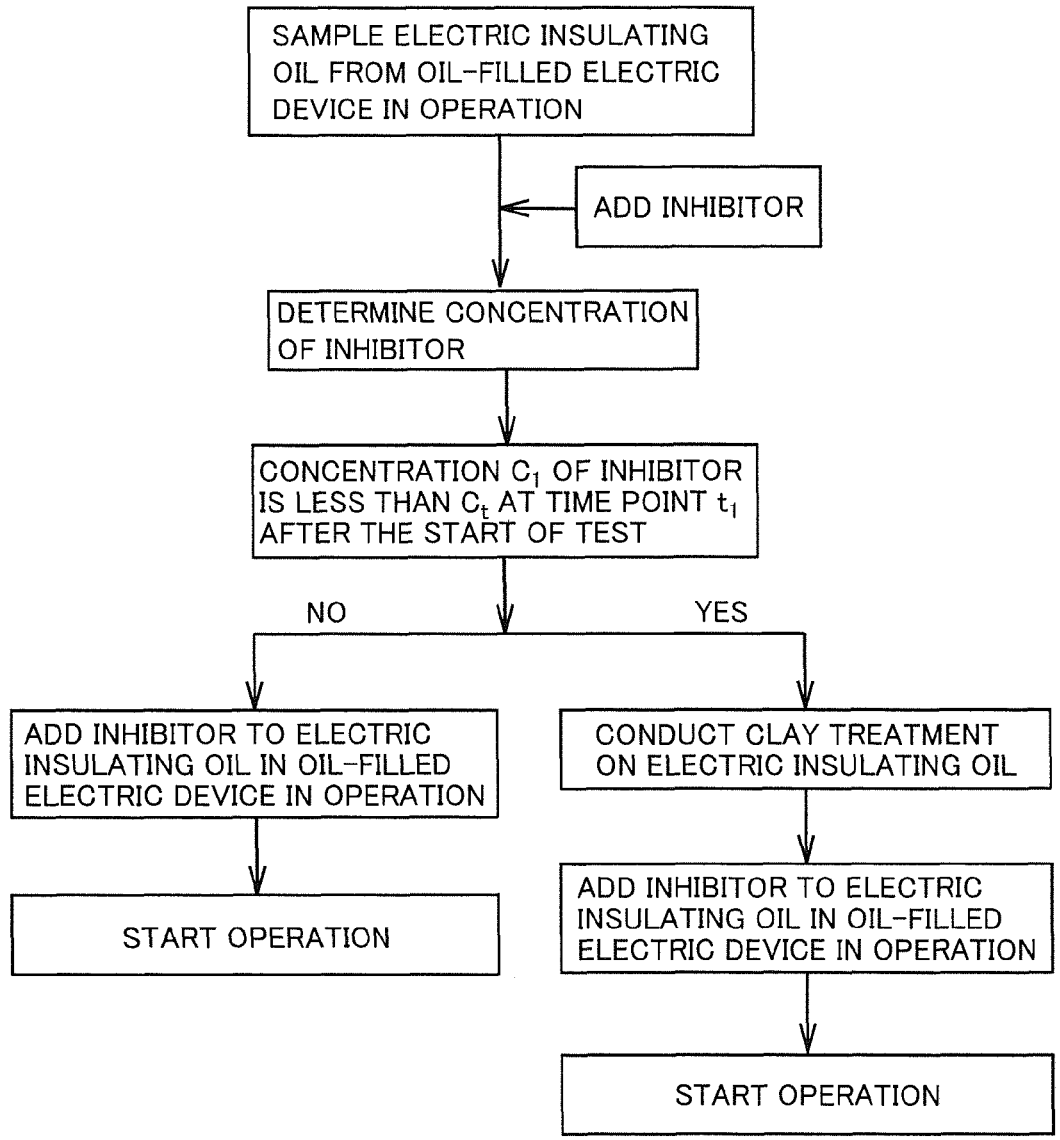
FIG. 1 is a flow chart illustrating a procedure of determining whether or not an inhibitor-consuming substance is present in an electric insulating oil according to Embodiment 1.

The electric insulating oil inspection method of the present invention is an inspection method for determining whether or not an inhibitor-consuming substance is present in an electric insulating oil. Herein, "inhibitor-consuming substance" refers to such a substance that causes a concentration of an inhibitor added to the electric insulating oil to decrease over time.

"inhibitor" is such a substance that is added to the electric insulating oil for the purpose of inhibiting the generation of copper sulfide on an insulating paper immersed in the electric insulating oil. As an example of the inhibitor, a benzotriazole compound may be given. Particularly, it is preferable to adopt a benzotriazole compound having a high oil solubility. As an example of such benzotriazole compound, 1, 2, 3-benzotriazole, Irgamet 39 (trade name) or the like may be given.

In the electric insulating oil inspection method of the present invention, the electric insulating oil is preserved at a predetermined condition and the concentration of the inhibitor is measured, and upon condition that a decrement of the concentration of the inhibitor relative to the initial concentration thereof becomes not less than a specified amount within a predetermined period, it is determined that the inhibitor-consuming substance is present.

The predetermined condition mentioned above may include a temperature condition, for example. In the inspection method of the present invention, it is preferable that a temperature in the temperature condition is higher than room temperature, because it is possible to attain a desired result quickly from a test in a short period. It is more preferable that the temperature in the temperature condition is not greater than 60° C. The reason is that if the temperature is greater than 60° C., the inhibitor decreases due to decomposition irrespective of the presence of the inhibitor-consuming substance, which makes it difficult to determine whether or not the inhibitor-consuming substance is present according to a decreasing tendency of the inhibitor.

As another condition, a lightproof condition may be given. Since the inhibitor decomposes upon exposure to light, it is preferable that a container for mixing the electric insulating oil and the inhibitor is lightproof.

As a method of measuring the concentration of the inhibitor, various publicly known methods for measuring substances in oil, for example, gas chromatography, GC-MASS, HPLC and the like may be adopted.

In the inspection method mentioned above, it is preferable to determine the inhibitor-consuming substance is present in the electric insulating oil upon condition that a decrease ratio of the concentration of the inhibitor in the electric insulating oil is greater than 10%. If the inhibitor-consuming substance is determined to be present in the electric insulating oil upon condition that the decrease ratio is equal to or less than 10%, it is highly possible to make a wrong determination due to measurement errors.

It is preferable that the inspection method mentioned above is conducted under such a condition that only the electric insulating oil is housed in the container without any other coexisting material such as copper coil, insulating paper or the like. If the other material which may react with the inhibitor or absorb the inhibitor is present in the container, it would be difficult to determine whether or not the inhibitor-consuming substance is present according to the decreasing tendency of the inhibitor.

[Electric Insulating Oil Treatment Method]

The present invention relates to an electric insulating oil treatment method in which whether or not an inhibitor-consuming substance is present in the electric insulating oil is preliminarily determined in accordance with the inspection method mentioned above, and a filtering treatment for removing the inhibitor-consuming substance from the electric insulating oil is conducted upon condition that the inhibitor-consuming substance is determined to be present.

The electric insulating oil treatment method may be preferably employed in adding the inhibitor against the generation of copper sulfide to the electric insulating oil (particularly the electric insulating oil in an operating oil-filled electric device). It is preferable that whether or not the inhibitor-consuming substance is present in the electric insulating oil is preliminarily determined in accordance with the inspection method mentioned above, a filtering treatment for removing the inhibitor-consuming substance from said electric insulating oil is conducted upon condition that the inhibitor-consuming substance is determined to be present, and the inhibitor is added to the electric insulating oil after the filtering treatment.

Particularly in overseas countries, it is needed to continuously use the electric insulating oil in a transformer through maintenance, and it is also possible to reduce the occurrence of environmental problems due to the large amount disposal of the electric insulating oil.

The filtering treatment mentioned above is not limited in particular if it is capable of removing the inhibitor-consuming substance from the electric insulating oil, and therefore various publicly known filtering treatments (treatment for removing impurities and the like by physical adsorption such as filtration or the like) may be adopted. For example, a clay treatment or a treatment employing porous materials such as activated charcoal and the like may be used. Particularly, the clay treatment is preferred. As the clay treatment, various publicly known methods (refer to, for example, Japanese Patent Laying-Open Nos. 59-23404, 59-217901 and 63-257112) may be adopted. It is preferable that clay used in the clay treatment is activated clay. Any commercially available clay, for example, white clay manufactured by Japan Activated Clay Co., Ltd may be used as the activated clay. As a detailed white clay treatment method, for example, the following method may be given: after the white clay is calcinated at 140° C. for 4 hours, it is added to the electric insulating oil by 5 wt % of the electric insulating oil, and after being kept in batch contact for 1 hour at 45° C., the white clay is filtered out.

[Oil-Filled Electric Device Maintenance Method]

The present invention also relates to an oil-filled electric device maintenance method employing the electric insulating oil treatment method mentioned above.

(Embodiment 1)

An embodiment of the electric insulating oil inspection method according to the present invention will be described. FIG. 1 is a flow chart illustrating a procedure of determining whether or not the inhibitor-consuming substance is present in the electric insulating oil.

Before adding the inhibitor against the generation of copper sulfide to the electric insulating oil, whether or not the inhibitor-consuming substance is present in the electric insulating oil is determined preliminarily. In accordance with the flow chart illustrated in FIG. 1, the electric insulating oil is sampled from the oil-filled electric device in operation, and after the inhibitor is added, the concentration of the inhibitor in the electric insulating oil is measured. If a concentration $C_1$ of the inhibitor is lower than a control value $C_t$ at a timing after $t_1$ has elapsed from the start of preservation, it is determined that the inhibitor-consuming substance is present in the electric insulating oil. In this case, after the electric insulating oil is subjected to the clay treatment, the inhibitor is added, and the operation of the oil-filled electric device is restarted. Alternatively, after the electric insulating oil is subjected to the clay treatment, the same inspection may be conducted again, and if it is determined that the inhibitor-consuming substance is absent in the electric insulating oil, the inhibitor may be added, and thereafter the operation of the oil-filled electric device may be restarted.

On the other hand, if $C_1$ is not lower than control value $C_t$, it is determined that the inhibitor-consuming substance is absent; thereby, the inhibitor is added to the electric insulating oil in the oil-filled electric device in operation, and the operation of the oil-filled electric device is restarted.

For example, if $t_1$ is 10 minutes, it is possible to set control value $C_t$ at a concentration (concentration where the percentage decrease of the concentration of the inhibitor is 10%) which is 90% of the initial concentration of the inhibitor.

Figure 2:
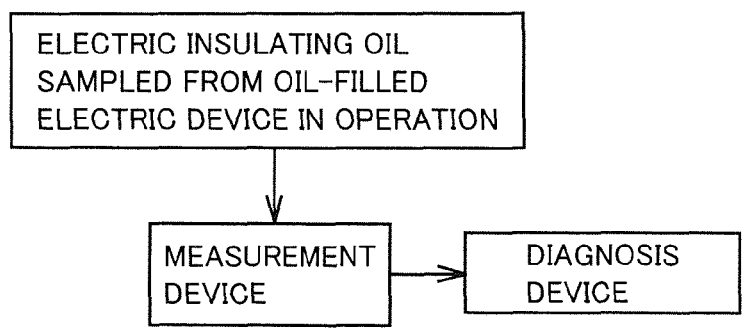
FIG. 2 is a block diagram of an inspection device employed in Embodiment 1.

FIG. 2 is a block diagram of an inspection device used in Embodiment 1. The inspection device illustrated in FIG. 2 is composed of a measurement device capable of conducting a measurement on the electric insulating oil sampled from the oil-filled electric device in operation and a diagnosis device capable of determining whether or not the inhibitor-consuming substance is present in the electric insulating oil on the basis of measured values by the measurement device. It is feasible to conduct the inspection method mentioned above by the use of the inspection device.

EXAMPLES

Hereinafter, the present invention will be described in detail with specific examples but not limited thereto.

Example 1

First, the electric insulating oil and the inhibitor (BTA) were mixed in a test container, and the inhibitor was stirred by a stirrer to dissolve in the electric insulating oil. Since the inhibitor reacts with light to decompose, a measuring flask which is auburn and lightproof was used as the test container. In addition, since the purpose of the present test is to determine whether or not the inhibitor-consuming substance is present, any coexisting material such as copper coil or the like which will react with the inhibitor is absent in the test container. The initial concentration of the inhibitor was 30 ppm.

As the electric insulating oil, 4 types of commercially available mineral oils for a transformer were adopted. Specifically, naphthenic mineral oils sampled from an oil-filled transformer after operation for 22 years and 27 years were adopted as an aged oil 1 and an aged oil 2, respectively. A naphthenic mineral oil obtained from a domestic petroleum maker was adopted as a fresh oil 3, and a naphthenic mineral oil obtained from an overseas maker was adopted as a fresh oil 4.

Thereafter, the test container was set in a thermostat and preserved at 40° C. which was a temperature close to an operation temperature of the oil-filled transformer. At each time point (time at day 1, 2, 4, 6, 10, 12, 15, 18 and 20) after the test container was set in the thermostat till 20 days had elapsed, electric insulating oils were each sampled from the test container periodically and the concentration of the inhibitor in each electric insulating oil was measured, and a temporal variation of concentrations was analyzed. The measurement of the concentration of the inhibitor was conducted by using HPLC.

Figure 3:
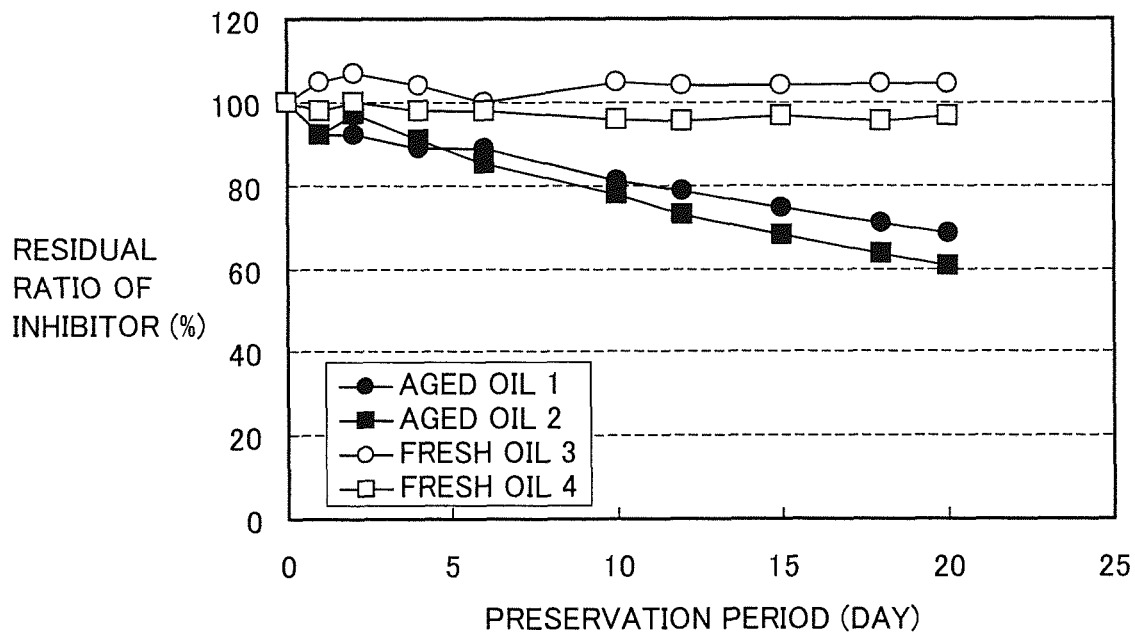
FIG. 3 is a graph illustrating an analysis result of Example 1.

The analysis result of the concentration of the inhibitor for each electric insulating oil mentioned above is shown in FIG. 3. In FIG. 3, the vertical axis represents a residual ratio of the inhibitor and the horizontal axis represents a preservation period. In addition, the concentration of the initially added inhibitor was set as 100%, and a ratio of the concentration of the sampled inhibitor relative to the initial concentration of the inhibitor was set as the residual ratio of the inhibitor.

As illustrated by FIG. 3, regarding aged oil 1 and aged oil 2, the concentration of the inhibitor in the electric insulating oil drops to 60% at day 20 after being heated; however, regarding fresh oil 1 and fresh oil 2, the concentration of the inhibitor in the electric insulating oil remains constant around 100% even after being heated for 20 days. On the basis of the result that the concentration of the inhibitor in the electric insulating oil decreases in the case of aged oils and the concentration of the inhibitor remains constant in the case of fresh oils, it is obvious that an inhibitor-consuming substance generated due to long-term deterioration is present in the electric insulating oil used in the oil-filled electric device.

Example 2

Similarly to Example 1 except that the preservation temperature in the thermostat was set at 60° C., the measurement and the analysis of the concentration of the inhibitor were conducted for each electric insulating oil mentioned above. The analysis result is shown in FIG. 4.

Figure 4:
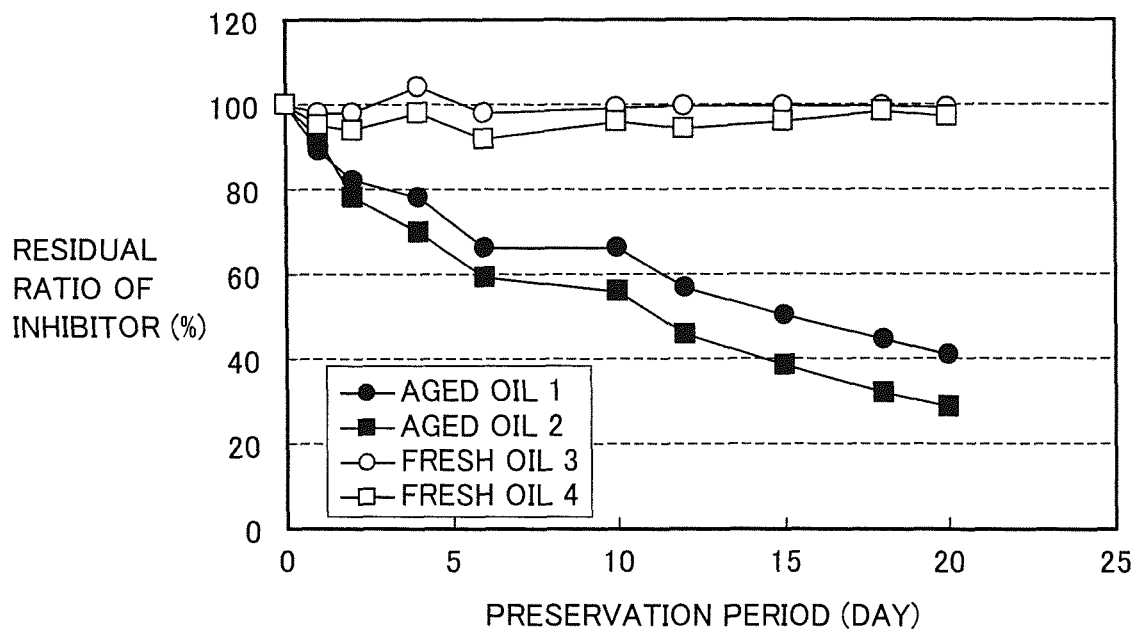
FIG. 4 a graph illustrating an analysis result of Example 2.

On the basis of the result illustrated by FIG. 4, similar to FIG. 3, since the concentration of the inhibitor in the electric insulating oil decreases in the case of aged oils and the concentration of the inhibitor remains constant in the case of fresh oils, it is obvious that an inhibitor-consuming substance generated due to long-term deterioration is present in the electric insulating oil used in the oil-filled electric device.

In the above test results, the analysis error was about 5%; thereby, if the decrease ratio of the concentration of the inhibitor with respect to the initial concentration after being preserved for a predetermined period is 10% or more, that is twofold of the analysis error, it is possible to determine that it is not the measurement error or the like but the inhibitor is decreasing significantly. In either FIG. 3 or FIG. 4, after 10 days from the start of preservation, the concentration of the inhibitor decreases at least 10% relative to the initial concentration. In accordance with the above descriptions, the electric insulating oil is preserved at a temperature higher than room temperature but not greater than 60° C., and after 10 days from the start of preservation, the concentration of the inhibitor in the electric insulating oil is measured. If the decrease ratio with respect to the initial concentration of the inhibitor is 10% or more, it is conceivable that the inhibitor-consuming substance is present in the electric insulating oil.

It should be understood that the embodiments and examples disclosed herein have been presented for the purpose of illustration and description but not limited in all aspects. It is intended that the scope of the present invention is not limited to the description above but defined by the scope of the claims and encompasses all modifications equivalent in meaning and scope to the claims.

The invention claimed is:

1. An electric insulating oil inspection method for determining whether or not an inhibitor-consuming substance is present in an electric insulating oil, said inhibitor-consuming substance being such a substance that causes to decrease over time a concentration of an inhibitor which is added to said electric insulating oil to inhibit generation of copper sulfide on an insulating paper immersed in said electric insulating oil, the electric insulating oil inspection method comprising:

a first step of preserving said electric insulating oil at a temperature of at least 40° C. but not higher than 60° C. and measuring the concentration of the inhibitor; and a second step of determining that the inhibitor-consuming substance is present in the electric insulating oil upon condition that a decrement of the concentration of the inhibitor relative to an initial concentration thereof becomes not less than a specified amount within a predetermined period, said inhibitor being a benzotriazole compound, and the inhibitor-consuming substance being determined to be present at said second step upon condition that a decrease ratio of the concentration of the inhibitor in the electric insulating oil after 10 days from the start of inspection is greater than 10%.

2. The inspection method according to claim 1, wherein said electric insulating oil is preserved at 40° C. at said first step.

3. The inspection method according to claim 1, wherein said first step is performed under such a condition that only said electric insulating oil is present in a container without any other coexisting material.

4. An electric insulating oil treatment method in which whether or not an inhibitor-consuming substance is present in an electric insulating oil is preliminarily determined in accordance with the inspection method according to claim 1, and a filtering treatment for removing the inhibitor-consuming substance from said electric insulating oil is performed upon condition that the inhibitor-consuming substance is determined to be present.

5. The electric insulating oil treatment method according to claim 4, wherein said filtering treatment is a clay treatment.

6. An oil-filled electric device maintenance method employing the electric insulating oil treatment method according to claim 4.

7. An electric insulating oil treatment method in which whether or not an inhibitor-consuming substance is present in an electric insulating oil is preliminarily determined in accordance with the inspection method according to claim 1 before adding to said electric insulating oil an inhibitor which inhibits generation of copper sulfide, a filtering treatment for removing the inhibitor-consuming substance from said electric insulating oil is performed upon condition that the inhibitor-consuming substance is determined to be present, and the inhibitor is added to said electric insulating oil after the filtering treatment.

* * * * *